United States Patent [19]

Stults

[11] Patent Number: 5,756,798

[45] Date of Patent: May 26, 1998

[54] PROCESS TO PREPARE ARYLDIPHOSPHORIC ESTERS

[75] Inventor: Jeffrey S. Stults, West Lafayette, Ind.

[73] Assignee: Great Lakes Chemical Corporation, West Lafayette, Ind.

[21] Appl. No.: 874,419

[22] Filed: Jun. 13, 1997

Related U.S. Application Data

[60] Provisional application No. 60/020,471 Jun. 13, 1996.

[51] Int. Cl.$^6$ .................................................... C07F 9/12
[52] U.S. Cl. ............................................. 558/99; 558/162
[58] Field of Search .................................................. 558/99

[56] References Cited

U.S. PATENT DOCUMENTS

| | | | |
|---|---|---|---|
| 2,520,090 | 8/1950 | Barrett | 260/461 |
| 3,254,973 | 6/1966 | Glammaria et al. | |
| 5,281,741 | 1/1994 | Gunkel et al. | 558/92 |
| 5,420,327 | 5/1995 | Bright et al. | 558/99 |

FOREIGN PATENT DOCUMENTS

| | | |
|---|---|---|
| 51-103195 | 9/1976 | Japan. |
| 64218 | 12/1974 | Romania. |
| 63976 | 2/1976 | Romania. |
| 71829 | 10/1977 | Romania. |
| WO 96/13508 | 5/1996 | WIPO. |
| WO 96/17853 | 6/1996 | WIPO. |

OTHER PUBLICATIONS

Database Caplus on STN, Chemical Abstracts, (Columbus, OH, USA) No. 117:235108, Tabankia et al. "Flame Retardant Polymer Compositions Containing Poly9butylene Terephthalate) and Oligomeric Phosphoric or Phosphonic Acid Esters" Abstract EP 491986, 1 Jul. 1992.

Janet R. Morrow et al., "Transesterfication of a Phosphate Diester by Divalent and Trivalent Metal Ions" *Inorganic Chemistry*, vol. 31, 1992, pp. 16–20.

Abstract: Jpn Kokai Tokkyo Koho JP 05186681, Jul. 1993, "Fire–resistant poly(phenylene ether) compositions."

Abstract: Brit. Patent No. 1027059, Apr. 1966, "Preparation and Uses of CN–1985 and CN–1986."

*Primary Examiner*—Michael G. Ambrose
*Attorney, Agent, or Firm*—Woodard, Emhardt, Naughton, Moriarty & McNett

[57] ABSTRACT

A process to prepare aryldiphosphate esters without forming an emulsion in the product is described. In one embodiment of this process, the ester is formed by initially reacting a phosphoryl oxyhalide with a dihydric aromatic compound in the presence of an insoluble catalyst to form an intermediate. The intermediate is then reacted with a monohydric aromatic compound in the presence of an insoluble catalyst to form the aryldiphosphate ester and the catalyst is then filtered from the aryldiphosphate ester. In another form of this process the ester is formed reacting a dihydric aromatic compound in the presence of an insoluble catalyst with a compound corresponding to the formula $(RO)_2POX$, where X is bromine or chlorine and R is an aromatic group and contains no more than 1 ortho substituent. Thereafter, the catalyst is then filtered from the aryldiphosphate ester.

12 Claims, No Drawings

PROCESS TO PREPARE ARYLDIPHOSPHORIC ESTERS

This application was based upon U.S. Provisional Application No. 60/020,471, filed Jun. 13, 1996.

This invention relates to processes that make bisaryl diphosphates, and more particularly relates to processes that make bisphenol A bis(diphenyl) phosphate.

BACKGROUND

Aryldiphosphate esters are known flame-retardants and the following formula generally represents their structure.

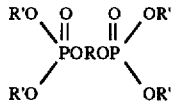

ORO is a dihydric phenol residue and the R's are the same or different aryl radicals.

Most any synthesis of these compounds requires a catalyst to accelerate the reactions to a practical level. For example, U.S. Pat. No. 5,281,741 to Gunkel describes the reaction of dihydroxy aromatic compounds with phosphorus oxychloride in nonaqueous solvent to form a diphosphotetrachloridate intermediate. The intermediate is then reacted with a monohydric aryl compound in the presence of a magnesium chloride catalyst to form the aryldiphosphate ester. Unfortunately this catalyst is slightly soluble in the product and must be removed by aqueous extraction, which leaves behind an undesirable emulsion.

Japanese Kokai Tokkyo Koho JP 05186681 teaches an alternate route with the same problem. The reference teaches the reaction of diphenylchlorophosphate with bisphenol A, also known as 4,4'-isopropylidenediphenol, to form bisphenol A bis(diphenyl)phosphate. The reaction requires high temperatures and an aluminum chloride catalyst. But this catalyst is also slightly soluble, and an emulsion forms when the catalyst is washed from the product.

These emulsions must either be removed with another process or left in the final product. A method is needed to prepare aryldiphosphate esters that does not form these emulsions, and this invention addresses that need.

SUMMARY OF THE INVENTION

In one aspect this invention is a process to prepare an aryldiphosphate ester by initially reacting a phosphoryl oxyhalide with a dihydric aromatic compound in the presence of an insoluble catalyst to form an intermediate. The intermediate is then reacted with a monohydric aromatic compound in the presence of an insoluble catalyst to form the aryldiphosphate ester. Thereafter, the catalyst is filtered from the product.

In another aspect, this invention is a process to prepare an aryldiphosphate ester by reacting a dihydric aromatic compound in the presence of an insoluble catalyst. The dihydric compound is reacted with a compound corresponding to the formula $(RO)_2POX$, where X is bromo or chloro and R is an aromatic that contains no more than 1 ortho substituent. Thereafter, the catalyst is then filtered from the aryldiphosphate ester.

An object of this invention is to synthesize aryldiphosphate esters without forming an emulsion when the catalyst is removed.

A feature of this invention is that the aryldiphosphate esters may be used as flame-retardants in organic polymers, and may particularly be used in polycarbonate-acrylonitrile-butadiene-styrene polymers.

An advantage of this invention is that high purity aryldiphosphate esters are formed without the need to remove water from them that would otherwise reside in the form of an emulsion.

DETAILED DESCRIPTION OF SOME PREFERRED EMBODIMENTS

We use specific language in the following description and examples to publicly disclose our invention and to convey its principles to others. No limits on the breadth of our patent rights based simply on using specific language is intended. We also include in our rights any alterations and modifications to our descriptions that should normally occur to one of average skill in this technology.

Generally, this invention is a catalytic process to synthesize an aryldiphosphate ester where the catalyst is filtered from the product, rather than washed. Furthermore, all necessary reactants and catalysts are widely known and commercially available to practice this invention.

In one embodiment, a phosphorus oxyhalide is initially reacted with a dihydric aromatic to form an intermediate, which is then reacted with a monohydric aromatic to form an aryldiphosphate ester. An insoluble catalyst is present during both reactions and is filtered from the product.

In the first step, the phosphorus oxyhalide is preferably phosphorus oxychloride, $POCl_3$, or phosphorus oxybromide, $POBr_3$. Either of which is also preferably used in excess. Preferable amounts range from one to five times the amount that is stoichiometrically required to complete the reaction. Alternatively, the amount of phosphorus oxyhalide may be reduced in order to form a mixture of monomeric, dimeric, trimeric, etc., materials to help maintain the fluidity of the final product.

Most any dihydric aromatic compound may be used in the first step, provided that no more than one substituent is ortho to each of the compound's aromatic hydroxyl groups. Suitable dihydric compounds include resorcinol, hydroquinone, bisphenol A, bisphenol S, bisphenol F, bisphenol methane, biphenols, and substituted dihydric aryl compounds. If a liquid aryldiphosphate is desired, then a nonsymmetrical or meta substituted dihydric aromatic compound should be used such as resorcinol.

Suitable catalysts for both steps of the synthesis include calcium chloride, calcium bromide, and group 1 halides such as sodium chloride, sodium bromide, potassium chloride, or potassium bromide. Presently, the most preferred catalyst is calcium chloride.

The first reaction is preferably performed at a temperature from about 90° C. to about 150° C. and continued until substantially all the dihydric compound is converted into the corresponding diphosphorotetrahalidate. Afterwards, it is desirable to remove any unreacted phosphorus oxyhalide before initiating the next reaction in order to minimize the formation of any triaryl-phosphates. For example, the oxyhalide may be removed by distillation with either low pressure (less than 20 torr) or high temperatures (120° C. to 200° C.). High temperatures are preferred because it is then easier to condense out the distilled phosphorus oxyhalide.

The second reaction may be preferably conducted with about four or more moles of any monohydric aromatic compound provided that the compound contains no more than one substituent ortho to the phenolic hydroxide. Suitable compounds include phenol, ortho-cresol, meta-cresol, para-cresol, xylenol (except 2,6-xylenol), 2-bromophenol, 3-bromophenol, 4-bromophenol, 2,4-dibromophenol, 2-chlorophenol, and 3-chlorophenol. Phenol is the presently preferred compound.

The second reaction is performed at a temperature suitable for the monohydric aromatic to react with the intermediate formed in the first reaction. One of average skill in this area should recognize that the particular temperature varies according to the substituents on both the dihydric aromatic compound used in the first reaction and the monohydric aromatic compound used in the second. Generally, monohydric aromatic compounds with ortho substituents require a higher temperature to react than monohydric aromatics with meta or para substituents. The preferred temperature range for reacting phenol with the intermediate is from about 160° C. to about 240° C. The reaction temperature may be held constant after the monohydric aromatic compound is added or the temperature may be raised in order to increase the rate of the second reaction.

It is further preferable that the monohydric compound is slowly added to the intermediate. A slow addition tends to minimize the formation of triarylphosphates. A preferred time range is minimally fifteen minutes up to about three hours.

An unexpected advantage of this process is that the reaction catalyst may be removed by filtration rather than by aqueous washings that would otherwise create an emulsion. Most any filter medium may be used to remove the catalyst such as diatomaceous earth or cake filtration with pressure or vacuum. During this step, it is preferable that the product is filtered at an elevated temperature. A preferable temperature range is from about 110° C. to about 240° C., and is more preferably from about 170° C. to about 190° C. Thereafter, any excess monohydric compound may be distilled from the ester product, or more preferably, removed with a wiped-film evaporator.

In another embodiment of this invention, the aryldiphosphate esters may be formed by reacting a compound of the formula $(RO)_2POX$, where X is bromo or chloro and R is aromatic, with the previously described dihydric aromatic compounds in the presence of the also previously described catalysts.

The $(RO)_2POX$ may be used either in a purified form or as a reaction mixture with the by-products, $(RO)POX_2$ and $(RO)_3PO$. These by-products are formed when the previously described phosphorus oxyhalides and monohydric aromatic compounds are reacted in the presence of the previously described catalysts to form the $(RO)_2POX$.

In this second embodiment, it is preferred that the dihydric aromatic compound is slowly added to the $(RO)_2POX$ at a temperature from about 150° C. to about 240° C. over a three to twelve hour period. A faster addition or one at a lower temperature may produce excessive amounts of triarylphosphates. The preferred temperatures and times range from about 180° C. to about 200° C. and occur over about an eight-hour period.

Preferably the $(RO)_2POX$ is present in the amount that is stoichiometrically required to react with all the dihydric aromatic compound. The reaction mixture is heated from about 150° C. to about 250° C. and allowed to react for a sufficient time to substantially convert all the $(RO)_2POX$ into its corresponding aryldiphosphate ester. Afterwards, the catalyst is filtered from the product as previously described.

EXAMPLES

Example 1

STEP 1

4,4'-Isopropylidenediphenol (607.5 g, 2.66 moles), phosphorus oxychloride (1455.7 g, 9.49 moles), and calcium chloride (29.89 g, 0.269 moles) were heated to reflux for 6.25 hours. Hydrogen chloride off-gas was trapped in water. Excess phosphorus oxychloride was removed at 110° C. under reduced pressure (700 torr to 25 torr) followed by increasing the reaction pot temperature to 180°–190° C. This material could be filtered to remove calcium chloride, decanted or used as is for the following step.

STEP 2

The intermediate bisphenol A tetrachlorodiphosphate (401.6 g, decanted from step 1), was heated to 180° C. and calcium chloride (25.2 g) was added. Phenol (307.5 g) was melted and placed in a heated addition funnel at 60° C. and added over 2.5 hours. Rapid gas evolution was seen upon addition of the phenol and it was necessary to melt some phenol from the condenser as the reaction proceeded. The reaction was heated at 180° C. for an additional 5.5 hrs, the temperature was raised to 220° C. and held there for 1 hour and then raised to 240° C. Additional phenol (1.8 g and 1.7 g) was added after 2.5 and 5 hours at 240° C. The material was heated for 1.5 hours after the final aliquot of phenol was added. The reaction mixture was cooled to 180° C., filtered through a coarse filter to remove catalyst, and placed on a rotovap at 188° C., 1 torr to remove minor amounts of phenol. The product (572 g) was poured from the flask to give a viscous, light yellow liquid, which was found to contain 81% monomer, bisphenol A tetraphenyl diphosphate, and 3.6% triphenyl phosphate.

EXAMPLE 2

The step 1 material from Example 1 (211.6 g) was treated in a similar manner except that phenol addition was conducted over 45 minutes and the reaction mixture was filtered through a medium fritted filter. The product was light colored, less viscous than the material from Example 1 and contained 7% triphenyl phosphate.

EXAMPLE 3

Diphenylchlorophosphate (199.4 g) and calcium chloride (13 g) were heated to 180° C. Bisphenol A (90.23 g) was added in approximately equal portions over 7 hours. Xylenes (20 ml) were added to the reactor and the reaction heated for an additional 18 hours. The mixture was cooled to 120° C. and filtered through a course sintered glass filter. The clear, slightly yellow product was placed on the rotovap at 95° C. and 20 torr for 1½ hours and then the pressure was lowered to 0.5 torr for an additional hour to give 240 g of product which contained 4% triphenyl phosphate.

EXAMPLE 4

Resorcinol (660 g), phosphorus oxychloride (3020.9 g) and calcium chloride (85.3 g) were reacted in the manner of example 1, step 1, and the product was decanted from the calcium chloride to give 1995 g of resorcinol diphosphorotetrachloridate. Resorcinol diphosphorotetrachloridate (321.4 g) and calcium chloride (18.2 g) were heated to 180° C. under a stream of nitrogen. Molten phenol (336.9 g) was added over 40 minutes. The reaction was heated at 180° C. for an additional 4 hours. The reaction temperature was raised to 240° C. and additional 3.3 g of phenol was added. Total time at 240° C. was 9 hours. The reaction was cooled to 180° C. and filtered through a medium sintered glass funnel. The material was placed on a rotatory evaporator at 186° C. and 1 torr for 1 hour. The product was poured from the flask and weighed 510 g.

Comparative Example

Diphenylchlorophosphate (61.5 g, 0.23 moles), bisphenol A (26.3 g, 0.115 moles) and magnesium chloride (0.34 g) were added together and heated to 180° C. over 1.3 hours and held there for an additional 4 hours. The reaction mixture was allowed to cool to 40° C. and was diluted with toluene (170 ml). The organic phase was washed with 50 ml 10% HCI followed by washing with a saturated aqueous sodium bicarbonate solution (100-ml). The organic and aqueous layers were very slow to separate with the total aqueous workup taking 6 hours. The organic phase was dried over magnesium sulfate, filtered, and the toluene removed under reduced pressure on a rotary evaporator to give a lightly colored, viscous liquid as product (75 g).

While we have attempted to illustrate and describe our invention in detail, please consider this as illustrative and not restrictive of our patent rights. The reader should understand that we have only presented our preferred embodiments and that all changes and modifications that come within the spirit of our invention are included if the following claims or the legal equivalent of these claims describes them.

We claim:

1. A process to prepare an aryldiphosphate ester, comprising:
    a) reacting a phosphoryl oxyhalide with a dihydric aromatic compound in the presence of a an insoluble catalyst to form a reaction product;
    b) reacting the reaction product of step a) with a monohydric aromatic compound in the presence of a catalyst to form the aryldiphosphate ester wherein the catalyst is insoluble in the aryldiphosphate ester, and
    c) filtering the catalyst from the aryldiphosphate ester.

2. The process of claim 1 wherein the catalyst is removed without an aqueous wash.

3. The process of claim 1 wherein the catalyst is a group 1 halide.

4. The process of claim 3 wherein the group 1 halide is sodium chloride, sodium bromide, potassium chloride or potassium bromide.

5. The process of claim 1 wherein the catalyst is a calcium halide.

6. The process of claim 5 wherein the calcium halide is calcium bromide or calcium chloride.

7. A process to prepare an aryldiphosphate ester, comprising:
    a) reacting a dihydric aromatic compound in the presence of a catalyst that is insoluble in the arydiphosphate ester with a compound corresponding to the formula $(RO)_2POX$, where X is bromo or chloro and R is an aromatic group and contains no more than 1 ortho substituent; and
    b) filtering the catalyst from the reaction media.

8. The process of claim 7 wherein the catalyst is removed without an aqueous wash.

9. The process of claim 7 wherein the catalyst is a group 1 halide.

10. The process of claim 9 wherein the group 1 halide is sodium chloride, sodium bromide, potassium chloride or potassium bromide.

11. The process of claim 7 wherein the catalyst is a calcium halide.

12. The process of claim 11 where the calcium halide is calcium bromide or calcium chloride.

* * * * *